United States Patent [19]
Sebillotte-Arnaud

[11] Patent Number: 5,728,389
[45] Date of Patent: Mar. 17, 1998

[54] SOLID COMPOSITION FOR CLEANSING THE SKIN, CONTAINING A PARTICULATE STRUCTURING AGENT

[75] Inventor: Laurence Sebillotte-Arnaud, Creteil, France

[73] Assignee: L'Oreal, Paris, France

[21] Appl. No.: 500,828

[22] Filed: Jul. 11, 1995

[30] Foreign Application Priority Data

Jul. 11, 1994 [FR] France ................................. 94 08565

[51] Int. Cl.⁶ ....................................................... A61K 9/00
[52] U.S. Cl. ............................. 424/400; 424/401; 424/61; 424/70.11; 424/70.19
[58] Field of Search ............................ 424/400, 401, 424/70.19, 61, 70.11

[56] References Cited

U.S. PATENT DOCUMENTS 3,645,904  2/1972  Beach .
4,536,405  8/1985  Nara et al. ................................. 424/60
4,963,535  10/1990  Debag et al. .............................. 424/47

FOREIGN PATENT DOCUMENTS

| 0 252 463 | 1/1988 | European Pat. Off. . |
| 0 254 612 | 1/1988 | European Pat. Off. . |
| 0 486 394 A1 | 5/1992 | European Pat. Off. . |
| 0 614 656 | 9/1994 | European Pat. Off. . |
| A-25 21 003 | 5/1975 | Germany . |
| A-94 14402 | 7/1994 | WIPO . |

*Primary Examiner*—Thurman K. Page
*Assistant Examiner*—D. Faulkner
*Attorney, Agent, or Firm*—Oblon, Spivak, McClelland, Maier & Neustadt, P.C.

[57] ABSTRACT

A skin cleansing composition containing, in a cosmetically acceptable medium, a structuring agent insoluble in this medium and formed of solid particles, which imparts a deformable solid appearance to the composition in which the medium is contained, this agent being capable of being removed from the skin using a diluent and the particles being at a concentration at least equal to the critical pigment charge volume.

22 Claims, No Drawings

SOLID COMPOSITION FOR CLEANSING THE SKIN, CONTAINING A PARTICULATE STRUCTURING AGENT

This application is a continuation of PCT-94-08565.

BACKGROUND OF THE INVENTION

Field of the Invention

The present invention relates to a novel cleansing composition for the skin, having a deformable solid appearance. On account of its extreme softness, this composition may be applied both to the face and to the body.

The invention also relates to a cosmetic treatment process for cleansing the skin.

The invention further relates to the use of a specific structuring agent in a skin cleansing composition.

Skin cleansing compositions are usually in the form of solid cakes such as soaps, or in the form of liquids that are viscous to a greater or lesser extent.

When a soap is used, the entire soap is made use of during each use, such that it gradually becomes soft through having been in contact with water, and it ages badly. In the end, it usually breaks and the user is left with small pieces of soap that are difficult to use. In addition, the softened soap is slippery, thereby making it difficult to use, especially for young children. As a result, it has become commonplace to use cleansing liquids instead of soaps. However, the more liquid the compositions, the harder it is to measure them out, since they tend to leak through the fingers. Moreover, the more liquid they are, the more likely they are to leak from their packaging.

In a simplified manner, a liquid cleansing composition comprises one or more surfactants in a cosmetically acceptable support containing water.

Each time a liquid cleansing composition has been used, it is necessary to rinse the cleansed skin afterwards. Unfortunately, a large number of liquid compositions have the drawback of being difficult to rinse off and/or of leaving traces of product on the skin.

Moreover, users are increasingly seeking novel product textures and new product concepts.

The subject of the present invention is, indeed, a novel skin cleansing composition which makes it possible in particular to overcome the drawbacks mentioned above. In particular, this composition is rinsed off in a noteworthy manner and has a quite uncommon texture. In addition, it is simple to apply and moistens perfectly in water.

SUMMARY OF THE INVENTION

The applicant has found, surprisingly, that it was possible to impart a deformable solid appearance to a skin cleansing composition by using an original structuring or texturing agent.

DETAILED DESCRIPTION OF THE INVENTION

Thus, the invention relates to a skin cleansing composition, characterized in that it contains, in a cosmetically acceptable medium, a structuring agent insoluble in this medium and formed of solid particles, which imparts a deformable solid appearance to the composition in which the medium is contained, this agent being capable of being removed from the skin using a diluent and the particles being at a concentration at least equal to the critical pigment charge volume.

Another subject of the invention is the use of a structuring agent in a skin cleansing composition in order to impart a deformable solid appearance thereto, this agent being formed of solid particles and being capable of being removed using a diluent and the particles being at a concentration at least equal to the critical pigment charge volume.

One of the advantages of this solid texture is that there is no risk of the composition of the invention escaping from its packaging, especially during transport. Moreover, this composition is very easy to handle and does not run between the fingers. It is much easier to measure out than the usual liquids. Furthermore, since the desired dose thereof may be taken during each use, there is no problem of it wearing out as with a soap.

According to the invention, the composition is of dry, deformable solid appearance, does not stain and resembles marshmallow (see document U.S. Pat. No. 3,682,659 for the consistency of marshmallow). This solid may be modelled like children's Plasticine. It may be broken readily by hand so as to take only the required amount of product. In particular, this composition may be packaged in single-dose form, which is particularly advantageous from the point of view of hygiene, and, for example, in the form of small cubes or beads or in sachet form.

By virtue of the particles of the invention, it is possible in particular to obtain a homogeneous (deformable solid) structure for constituents which normally lead to two separate phases (immiscible constituents, for example oil/water).

For the purpose of obtaining a solid which feels soft and pleasant, it is preferable to use particles having a particle size of from 1 µm to 300 µm, for example from 5 µm to 200 µm and preferably from 10 µm to 100 µm and better still from 15 µm to 40 µm.

The great softness provided by these particles allows the cleansing composition of the invention to be used by individuals with sensitive skin.

In order to impart a light and airy appearance to the composition of the invention, particles having a density of less than 0.09 and better still of less than 0.06 and even better still of less than 0.04 are advantageously used.

For the purpose of obtaining this low density, hollow particles filled with a gas are advantageously used. This gas may be air, nitrogen, isobutane, isopentane, etc.

According to another advantageous characteristic of the invention, the particles are in the form of beads. It is, however, possible to use particles in the form of fibres.

These particles may be made of various inert materials which do not react chemically with the cosmetically acceptable medium or support; in particular, these particles do not react with the oils, the surfactants, the water and the various other constituents of the composition, such as the active agents.

The texturing agent of the invention has the particular feature of being readily removed from the skin by simple dilution. It acts, in fact, as a vehicle or reservoir for the cosmetic support. It moreover enables the support and especially the active agent or agents, contained in the deformable solid, to be recovered, when necessary, by simple dilution with water. This is probably due to the fact that the cosmetic support is housed in the interparticulate spaces of the solid and not in the particles.

Besides water, water charged with salts may also be used as diluent.

As a selection criterion for the texturing agent, the following test may be performed:
- addition of determined particles in water containing a dye conventionally used in the field of cleansing, such as the disodium salt of brilliant blue FCF catalogued in the Color Index under the reference CI 42090, until a coloured paste is obtained,
- pouring of a drop of water onto the paste.

When the paste is much clearer at the point of impact of the drop of water than the rest of the paste, this means that the particles in question are candidates for texturing agent. On the other hand, when the paste is not decolorized at the point of impact, the particles in question are not at all suitable.

The inert particles are advantageously made of thermoplastic materials, for instance polyamides such as nylon, polymers or copolymers of acrylonitrile, of vinylidene chloride, of vinyl chloride and/or of acrylic or styrene monomer, which may be expanded. The acrylic monomer is, for example, a methyl or ethyl acrylate or methacrylate. The styrene monomer is, for example, α-methylstyrene or styrene.

Nylon particles which may be used are the "Orgasol" particles sold by the company Atochem. These particles are porous solid spheres of diameter ranging from 5 μm to 60 μm.

The particles are preferably hollow deformable particles of an expanded copolymer of vinylidene chloride and acrylonitrile or of vinylidene chloride, acrylonitrile and methacrylate. It is possible, for example, to use a copolymer containing: from 0% to 60% of units derived from vinylidene chloride, from 20% to 90% of units derived from acrylonitrile and from 0% to 50% of units derived from an acrylic or styrene monomer, the sum of the percentages (by weight) being equal to 100. These particles are especially in the dry or hydrated state and may be obtained, for example, according to the processes described in the patents and patent applications EP-A-56,219, EP-A-348,572, EP-A-320, 473, EP-A-112,807 and U.S. Pat. No. 3,615,972.

These hollow particles may, for example, be those formed of a terpolymer of vinylidene chloride, acrylonitrile and methacrylate, sold under the trade name EXPANCEL by the company Nobel Casco under the references 551 DE 12 (particle size of approximately 12 μm and specific gravity of 40 kg/m$^3$), 551 DE 20 (particle size of approximately 30 μm and specific gravity of 65 kg/m$^3$) and 551 DE 50 (particle size of approximately 40 μm). There may also be mentioned microspheres formed of the same expanded terpolymer in the dry state, having a particle size of approximately 18 μm and a specific gravity of approximately 60 to 80 kg/m$^3$, referred to below as EL 23, or having a particle size of approximately 34 μm and a specific gravity of approximately 20 kg/m$^3$, referred to below as EL 43, and having a particle size of approximately 150 μm, referred to below as EL 55.

As other hollow polymer particles which may be used in the invention, there may also be mentioned the polymers and the copolymers obtained from the itaconic, citraconic, maleic and fumaric acids and from vinyl acetate or lactate esters (see in this regard document JP-A-2,112,304), or alternatively non-expanded copolymer particles of vinylidene chloride and acrylonitrile or of vinylidene chloride, acrylonitrile and methacrylate, sold under the trade name EXPANCEL with the reference 551 WU.

In contrast, particles of corn starch, pyrogenous silica or of non-expanded polyester, polyurethane or polyethylene do not make it possible to obtain a solid composition which is removed well from the skin during rinsing.

It is, admittedly, known to modify the viscosity of a liquid medium with solid particles (see on this subject the article Elsevier Sequoia, 1992, Progress in Organic Coatings, 21, p. 255–267, from A. Toussaint "Choice of rheological model for steady flow: application to industrial concentrated suspensions") but nobody to date has either described or suggested the use of the solid product, obtained from a certain concentration of particles, in the field of cleansing in order to store the medium in which the particles are dispersed.

In other words, the production or otherwise of the deformable solid is linked to the amount of structuring agent used in the composition; above a certain quantity of particles, referred to as the critical pigment charge volume and abbreviated to CPCV, a sudden increase in the viscosity of the medium is observed. The CPCV is a function of the medium and of the nature of the particles; it must thus be determined every time. Its determination poses no problem to those skilled in the art. It is possible, for example, to use the official ASTM method in order to determine the CPCV.

Another subject of the invention is the use of the composition defined above for cleansing the skin.

Thus, another subject of the invention is a skin cleansing process, consisting in applying a composition as defined above to the skin, and then in rinsing the skin.

The composition of the invention contains, besides the texturing particles, all the constituents conventionally used in cleansing compositions. These constituents are, in particular, mineral, plant, synthetic or silicone-containing oils, water, screening agents, fragrances, foaming and/or cleansing surfactants, polymers, preserving agents, antioxidants, pH regulators, sequestering agents, fillers, etc.

The composition according to the invention may in particular contain one or more cleansing and/or foaming surfactants, which may be nonionic, anionic and/or amphoteric surfactants, and which may be used in an amount ranging, for example, from 5% to 60% by weight, and preferably from 10% to 40% by weight, relative to the total weight of the composition.

Nonionic surfactants which may be mentioned, for example, are alkylphenol oxide condensates, condensates of ethylene oxide, of propylene oxide and of ethylenediamine, alkylpolyglucosides, fatty acid polyethylene glycol glyceryl esters such as, for example, polyglyceryl-3 hydroxylauryl ether (CTFA name) sold under the name CHIMEXANE NF by the company Chimex.

Anionic surfactants which may be mentioned, for example, are fatty alcohol polyalkylene glycol ethers such as, for example, taurates, acyl lactylates, alkyl sulphates, polyoxyethylenated alkyl sulphates, alkyl ether sulphates, alkyl ether carboxylates, monoalkyl or dialkyl phosphates and ethoxylated alkyl phosphates, N-acyl sarcosinates, N-acyl glutamates, acyl isethionates, polysorbates and succinamates.

Amphoteric or zwitterionic surfactants which may be mentioned, for example, are betaines and betaine derivatives, sultaines and sultaine derivatives, and imidazolinium derivatives.

Silicone-containing surfactants may also be used in the compositions according to the invention. Silicone-containing surfactants which may be mentioned are polydimethylsiloxanes containing glucoside groups, such as SLM SPG 120 from the company Wacker, or alternatively polydimethylsiloxane derivatives containing alkyl phosphobetaine groups, such as PECOSIL SPB-1240 from the company U. C. I. B.

The composition according to the invention may additionally contain oils, which may be used in an amount ranging from 0% to 30% by weight, and preferably from 0% to 10% by weight, relative to the total weight of the composition.

The oils used in the compositions according to the invention may be chosen, for example, from mineral oils such as paraffin oil and liquid petrolatum; oils of animal origin such as perhydrosqualene; oils of plant origin such as sweet almond oil, avocado oil, castor oil, olive oil, jojoba oil, sesame oil, groundnut oil, grapeseed oil, rapeseed oil, coconut oil, hazelnut oil, karite butter and the liquid fraction thereof, palm oil, apricot kernel oil, calophyllum oil, rice bran oil, corngerm oil, wheatgerm oil, soya oil, sunflower oil, safflower oil, passion flower oil and rye oil; synthetic oils such as fatty esters, for instance purcellin oil, butyl myristate, isopropyl myristate, hexadecyl stearate, isopropyl stearate, octyl stearate, isodecyl stearate, decyl oleate, hexyl laurate and propylene glycol dicaprylate, and esters derived from lanolic acid, for instance isopropyl lanolate and isocetyl lanolate, isoparaffins, acetylglycerides, octanoates of alcohols and of polyalcohols such as those of glycol and of glycerol, ricinoleates of alcohols and of polyalcohols, and fatty acid triglycerides; silicone oils such as cyclomethicones, volatile and/or non-volatile polydimethylsiloxanes or alternatively phenyldimethylsiloxanes.

Furthermore, in a known manner, the cleansing compositions of the invention may contain adjuvants that are common in the field of cleansing of the skin, such as hydrophilic or lipophilic active agents, preserving agents, antioxidants, fragrances and dyes. These adjuvants are used in the usual proportions for cleansing compositions and, for example, from 0.01 to 10% by weight relative to the total weight of the composition.

Hydrophilic or lipophilic active agents which may be mentioned, for example, are hydrating agents such as polyols, and in particular glycerol, antibacterial agents such as octopirox and triclosan, and keratolytic agents such as salicylic acid.

The examples below are given as an illustration and without any limitation, in order for the characteristics of the invention to emerge more clearly.

EXAMPLE 1

Cleansing composition for greasy skin with a tendency towards acne (CTFA nomenclature)

| Phase A | |
|---|---|
| Sodium laureth sulphate (Texapon N70 sold by the company Henkel) (anionic surfactant) | 12.5% |
| Disodium cocoamphodiacetate (Concentrated Miranol C2M sold by the company Rhône-Poulenc) (amphoteric surfactant) | 4.3% |
| Sodium cocoyl isethionate/sodium isethionate (90/10) (Gerapon AC78 sold by the company Rhône-Poulenc) (anionic surfactant) | 0.8% |
| Glycerol | 3.0% |
| Preserving agent qs | |
| Demineralized water qs | 100% |
| Phase B | |
| Liquid fraction of karite butter | 2.0% |
| Octopirox (antibacterial agent) | 0.1% |
| Fragrance qs | |
| Salicylic acid (keratolytic agent) | 0.5% |
| Phase C | |
| EXPANCEL 551 DE 20 | 14.0% |

The procedure consists in mixing together the various constituents of phase A, in heating if necessary, in order to obtain a homogeneous phase, in adding phase B thereto, and then in homogenizing the mixture and in adding phase C thereto with mixing until a homogeneous paste is obtained.

A white paste is obtained which is non-sticky, easily modellable, easy to moisten, easy to apply and to remove, feels soft and has good foaming power.

EXAMPLE 2

Cleansing composition for greasy skin with a tendency towards acne (CTFA nomenclature)

| Phase A | |
|---|---|
| PEG-120 methylglucose dioleate (Glucamate DOE 120 sold by the company Amerchol) (nonionic surfactant) | 3.5% |
| Sodium lauroyl sarcosinate (Oramix L30 sold by the company Seppic) (anionic surfactant) | 14.5% |
| Disodium laureth sulphosuccinate (Setacin 103 Special sold by the compnay Zchimmer Schwarz) (anionic surfactant) | 2.4% |
| Lauramide DEA (Comperlan LMD sold by the company Henkel) (nonionic surfactant) | 2.0% |
| Demineralized water | qs 100% |
| Phase B | |
| Corngerm oil | 2.5% |
| Octopirox (antibacterial agent) | 0.2% |
| Lactic acid | qs pH 7 |
| Phase C | |
| EXPANCEL 551 DE 20 | 8.0% |

The procedure is the same as for the above example, and a paste having similar properties is obtained.

EXAMPLE 3

Cleansing composition for any skin type (CTFA nomenclature)

| Phase A | |
|---|---|
| Sodium laureth sulphate (Texapon N70 sold by the company Henkel) (anionic surfactant) | 14% |
| Disodium cocoamphodiacetate (Concentrated Miranol C2M sold by the company Rhône-Poulenc) (amphoteric surfactant) | 5% |
| Sodium cocoylisethionate (Hostapon SCI sold by the company Hoechst) (anionic surfactant) | 1% |
| Hydrogenated Talloweth-60 myristyl glycol (Elfacos GT 282 S sold by the company Akzo) (nonionic surfactant) | 2% |
| Demineralized water qs | 100% |
| Phase B | |
| Liquid fraction of karite butter | 3% |
| Phase C | |
| EXPANCEL 551 DE 20 | 11% |

The procedure is the same as for Example 1, and a paste having similar properties is obtained.

EXAMPLE 4

Cleansing composition for sensitive skin (CTFA nomenclature)

| Phase A | |
|---|---|
| Sodium lauroyl sarcosinate (Oramix L30 sold by the company Seppic) (anionic surfactant) | 7.0% |
| Disodium laureth sulphosuccinate (Setacin 103 Special sold by the company Zchimmer Schwarz) (anionic surfactant) | 2.4% |
| Glycerol | 5.0% |
| Demineralized water qs | 100% |
| Phase B | |
| Sweet almond oil | 1.0% |
| Phase C | |
| EL 23 microspheres | 10.5% |

The procedure is the same as for Example 1, and a paste having similar properties is obtained.

EXAMPLE 5

Cleansing composition for any skin type (CTFA nomenclature)

| Phase A | |
|---|---|
| Sodium laureth sulphate (Texapon N70 sold by the company Henkel) (anionic surfactant) | 14% |
| Disodium cocoamphodiacetate (Concentrated Miranol C2M sold by the company Rhône-Poulenc) (amphoteric surfactant) | 5% |
| Glycerol | 3% |
| Demineralized water qs | 100% |
| Phase B | |
| Dimethicone (Silbione Oils 70047 V 300 sold by the company Rhône-Poulenc) (oil) | 2% |
| Phase C | |
| Nylon 12 (Orgasol 2002 D Nat Co sold by the company Atochem) | 44% |

The procedure is the same as for Example 1, and a paste having similar properties is obtained.

EXAMPLE 6

Cleansing composition for any skin type (CTFA nomenclature)

| Phase A | |
|---|---|
| Polyglyceryl-3 hydroxylauryl ether (Chimexane NF sold by the company Chimex) (nonionic surfactant) | 6% |
| Sodium laureth sulphate (Texapon N70 sold by the company Henkel) (anionic surfactant) | 12% |
| Demineralized water qs | 100% |
| Phase B | |
| Dimethicone (Silbione Oils 70047 V 300 sold by the company Rhône-Poulenc) (oil) | 1% |
| Phase C | |
| EXPANCEL 551 DE 20 | 8% |

The procedure is the same as for Example 1, and a paste having similar properties is obtained.

EXAMPLE 7

Cleansing composition for very dry skin (CTFA nomenclature)

| Phase A | |
|---|---|
| Polyglyceryl-3 hydroxylauryl ether (Chimexane NF sold by the company Chimex) (nonionic surfactant) | 10% |
| Triclosan (antibacterial agent) | 1% |
| Demineralized water qs | 100% |
| Phase B | |
| Liquid fraction of karite butter | 2% |
| Caprylic/capric triglyceride | 5% |
| Phase C | |
| EL 23 microspheres | 8% |

The procedure is the same as for Example 1, and a paste having similar properties is obtained.

What is claimed as new and is desired to be secured by Letters Patent of the United States is:

1. A skin cleansing composition containing a cosmetically acceptable medium and a structuring agent insoluble in said medium and formed of particles, said particles imparting a deformable solid appearance to said composition, said agent being capable of being removed from the skin using a diluent, and wherein said particles are present at a concentration at least equal to the critical pigment charge volume.

2. The composition according to claim 1, wherein the particles have a particle size of from 1 μm to 300 μm.

3. The composition according to claim 1, wherein the particles have a particle size of from 10 μm to 100 μm.

4. The composition according to claim 1, wherein the particles have a density of less than 0.09.

5. The composition according to claim 1, wherein the particles have a density of less than 0.04.

6. The composition according to claim 1, wherein the particles are hollow.

7. The composition according to claim 1, wherein the particles are made of a thermoplastic material.

8. The composition according to claim 1, wherein the particles are made of material selected from the group consisting of nylon, polymers and copolymers of vinylidene chloride, of vinyl chloride, of acrylonitrile and/or of an acrylic or styrene monomer.

9. The composition according to claim 1, wherein the particles are hollow particles of an expanded copolymer of vinylidene chloride and acrylonitrile, or of an expanded copolymer of vinylidene chloride, acrylonitrile and an acrylic or styrene monomer.

10. The composition according to claim 1, which additionally contains at least one foaming and/or cleansing surfactant.

11. A process for cleansing the skin which comprises applying the composition of claim 1 to the skin.

12. The process according to claim 11, additionally comprising lathering the composition and then rinsing it from the skin.

13. A process of imparting a deformable solid appearance to a cleansing composition, comprising adding thereto a structuring agent, said agent being formed of solid particles and being capable of being removed using a diluent and said particles being at a concentration at least equal to the critical pigment charge volume.

14. The process according to claim 13, wherein the particles have a particle size ranging from 1 μm to 300 μm.

15. The process according to claim 13, wherein the particles have a particle size ranging from 10 µm to 100 µm.

16. The process according to claim 13, wherein the particles have a density of less than 0.09.

17. The process according to claim 13, wherein the particles have a density of less than 0.04.

18. The process according to claim 13, wherein the particles are hollow.

19. The process according to claim 13, wherein the particles are made of a thermoplastic material.

20. The process according to claim 13, wherein the particles are made of a material selected from the group consisting of nylon, polymers and copolymers of vinylidene chloride, of vinyl chloride, of acrylonitrile and/or of an acrylic or styrene monomer.

21. The process according to claim 13, wherein the particles are hollow particles of an expanded copolymer of vinylidene chloride and acrylonitrile, or of an expanded copolymer of vinylidene chloride, acrylonitrile and an acrylic or styrene monomer.

22. The process according to claim 13, wherein the composition additionally contains at least one foaming and/or cleansing surfactant.

* * * * *